US011815488B2

(12) United States Patent
Kimzey et al.

(10) Patent No.: US 11,815,488 B2
(45) Date of Patent: Nov. 14, 2023

(54) USE OF TRI- AND TETRA-HYDROXYL QUATERNARY AMMONIUM COMPOUNDS AS RESOLVING AGENTS FOR ELECTROPHORETIC SEPARATIONS

(71) Applicant: Agilent Technologies, Inc., Santa Clara, CA (US)

(72) Inventors: Michael J. Kimzey, Laguna Hills, CA (US); Fielito U. Limjap, Manila (PH); Francis T. Haxo, San Francisco, CA (US); Sergey Vlasenko, Davis, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 558 days.

(21) Appl. No.: 16/960,307

(22) PCT Filed: Jan. 11, 2019

(86) PCT No.: PCT/US2019/013365
§ 371 (c)(1),
(2) Date: Jul. 6, 2020

(87) PCT Pub. No.: WO2019/140314
PCT Pub. Date: Jul. 18, 2019

(65) Prior Publication Data
US 2020/0371063 A1 Nov. 26, 2020

Related U.S. Application Data

(60) Provisional application No. 62/617,110, filed on Jan. 12, 2018.

(51) Int. Cl.
*G01N 27/447* (2006.01)
*C12N 15/10* (2006.01)

(52) U.S. Cl.
CPC ..... *G01N 27/44747* (2013.01); *C12N 15/101* (2013.01); *G01N 27/44791* (2013.01)

(58) Field of Classification Search
None
See application file for complete search history.

(56) References Cited

U.S. PATENT DOCUMENTS

| | | | |
|---|---|---|---|
| 4,654,132 A | 3/1987 | Takagi | |
| 2007/0161116 A1 | 7/2007 | Copse | |
| 2009/0111726 A1 | 4/2009 | Shang et al. | |
| 2009/0203566 A1 | 8/2009 | Lee et al. | |
| 2016/0356783 A1 | 12/2016 | Parsons et al. | |
| 2017/0158993 A1 | 6/2017 | Ivanov et al. | |
| 2019/0169230 A1* | 6/2019 | Kimzey | C07K 1/113 |

FOREIGN PATENT DOCUMENTS

| | | |
|---|---|---|
| CN | 106398581 A | 2/2017 |
| CN | 106536668 A | 3/2017 |
| JP | 61-36296 A | 2/1986 |
| JP | 62022796 A | 1/1987 |
| JP | S6222796 A | 1/1987 |
| JP | 06118058 A | 4/1994 |
| JP | 200671433 A | 3/2006 |
| JP | 2007516449 A | 6/2007 |
| JP | 2017-529318 A | 5/2017 |
| WO | WO 2005/064325 A2 | 7/2005 |
| WO | WO2016/011329 A1 | 1/2016 |
| WO | WO02017/041013 A1 | 3/2017 |

OTHER PUBLICATIONS

Machine Translation to English for JP S62-22796 A (Year: 1987).*
Durney, BC et al., Capillary Electrophoresis Applied to DNAL Determining and Harnessing Sequence and Structure to Advance . . . , Anal Bioanal Chem, 2015, pp. 6923-6938, vol. 407.
Thomas, Shane, International Search Report, PCT/US 19/13365, ISA/US, dated Mar. 15, 2019.
Thomas, Shane, Written Opinion, PCT/US 19/13365, ISA/US, dated Mar. 15, 2019.
Michalitsch, R., Supplementary European Search Report, EP19738725. 1, dated Sep. 27, 2021, European Patent Office, Munich, Germany.
Author Unknown, Global Dossier bibliographic information and English abstract of CN 106398581A, EPO Espacenet website.
[Author Name Not in English] Radiation prep. and prop. of 3-chloro-2-hydroxypropyl trimethylammonium . . . , J Wuhan Univ, Nat Sci Ed., 2016, doi:10.14188/j.1671-8836.2016.0.

* cited by examiner

*Primary Examiner* — J. Christopher Ball
(74) *Attorney, Agent, or Firm* — Laurence J. Hyman; Hyman IP Law (57) ABSTRACT

The present disclosure provides methods of improving the resolution of analytes by in electrophoretic separations using a gel by incorporating into the gel an effective amount of one or more tri- or tetra-hydroxyl quaternary ammonium compounds, or a mixture of such compounds.

20 Claims, 2 Drawing Sheets

Fig. 1a – Separation of APTS-labeled glycans released from Enbrel® using a standard gel Fig. 1b – Separation of APTS-labeled glycans released from Enbrel® using same gel, but containing THMH Fig. 2a – Injection 2 – Separation of InstantQ™-labeled glycans released from human IgG, using THMH gel in a PVA-coated capillary Fig. 2b – Injection 235 – Separation of InstantQ™-labeled glycans released from human IgG, using THMH gel in a PVA-coated capillary

USE OF TRI- AND TETRA-HYDROXYL QUATERNARY AMMONIUM COMPOUNDS AS RESOLVING AGENTS FOR ELECTROPHORETIC SEPARATIONS

CROSS-REFERENCE TO RELATED APPLICATIONS

This is a national stage application under 35 U.S.C. § 371 of International Application No. PCT/US2019/013365, filed Jan. 11, 2019, which is hereby incorporated by reference for all purposes. This application further claims priority to U.S. Provisional Patent Application No. 62/617,110, filed Jan. 12, 2018, the contents of which are incorporated herein for all purposes.

STATEMENT OF FEDERAL FUNDING

Not applicable.

BACKGROUND OF THE INVENTION

This invention relates to the field of analysis of analytes by subjecting a gel containing such analytes to separation by electrophoresis.

In electrophoresis, analytes are subjected to an electric force which causes the analytes to migrate through the gel. Typically, the analyte or analytes of interest are labeled to facilitate their detection and quantitation after their separation from other components present in the sample.

One family of techniques for analyzing various analytes present in a sample is electrophoresis. Typically, samples comprising the analyte or analytes of interest are loaded onto a gel and subjecting the analytes in the sample to an electric potential across the length of the gel, causing them to move through the gel. A number of forms of electrophoretic separations are known in the art. These include, but are not limited to, slab gel, capillary electrophoresis ("CE"), electrofiltration, Differential In-gel Electrophoresis ("DIGE"), zone electrophoresis, Isoelectric Focusing ("IEF"), native electrophoresis, 2-dimensional electrophoresis, immunochemical/immunofixation electrophoresis, immobilized pH gradient electrophoresis, microchips, moving boundary, isotachophoresis, pulse-field electrophoresis, as well as combinations of these. Within capillary electrophoresis, techniques include capillary gel electrophoresis, or "CGE," which separates molecules based on molecular size, and capillary zone electrophoresis, or "CZE," which separates molecules based on charge:mass ratio.

CE, CGE and CZEE are well known in the art and are taught extensively in the literature, including Beckman Coulter's booklet "Introduction to Capillary Electrophoresis" (undated, but from 1991-2), Whatley, H., Basic Principles and Modes of Capillary Electrophoresis, in Petersen and Mohammad, eds., Clinical and Forensic Applications of Capillary Electrophoresis, Humana Press, Inc. Totowa, N.J. (2001), and Lauer and Rozing, eds., High Performance Capillary Electrophoresis, 2$^{nd}$ Ed., Agilent Technologies, Inc., Santa Clara, Calif. (2014). CGE has been used for decades to separate proteins and nucleic acids. See, e.g., Zhu et al., Anal Chim Acta. 2012 Jan. 4; 709: 21-31.

Different electrophoretic techniques can be used to separate various types of compounds. Separation of glycans from one another, and particularly separation of N-glycans by electrophoretic techniques has been more challenging than separating proteins or nucleic acids from one another, due to the respective characteristics of these types of compounds. See, e.g., Schwarzer, et al., "N-glycan analysis by CGE-LIF: Profiling influenza A virus hemagglutinin N-glycosylation during vaccine production," Electrophoresis 2008, 29, 4203-4214, at 4204. Typically, glycans to be analyzed by CGE are labeled with a charged fluorophore or a UV-visible dye to allow detection by, for example, laser induced fluorescence ("LIF") or by UV light. See, e.g., Schwarzer, supra, Reusch, et al., "High-throughput glycosylation analysis of therapeutic immunoglobulin G by capillary gel electrophoresis using a DNA analyzer," 2014, doi: 10.4161/mabs.26712.

Detection systems for electrophoretic separations may include absorbance, fluorescence, mass spectrometry, conductivity, potentiometry, or amperometry. Accurate detection and quantitation of the analyte or analytes of interest may, however, be rendered difficult due to the presence of other compounds present in the sample which co-migrate with the analyte of interest under the conditions under which the electrophoretic separation is performed. Reducing such co-migration would improve resolution of the analytes of interest present in the sample being analyzed. To date, compositions and methods for reducing co-migration of components of a sample undergoing electrophoretic separation, and thus for improving resolution of the analytes of interest from other components in the sample, have not been reported.

There remains a need for compositions and methods that improve resolution of analytes and components, and particularly of glycans, that co-migrate together during electrophoretic separations, such as CE or CGE. Surprisingly, the present invention meets these and other needs.

BRIEF SUMMARY OF THE INVENTION

The invention provides compositions, methods, systems, and kits, for improving the separation of labeled analytes by electrophoresis. In a first group of embodiments, the invention provides gels for electrophoretic separation of analytes. The gels comprise one or more compounds of structure 1, or one or more compounds of structure 2, or a mixture of one or more compounds of structure 1 and one or more compounds of structure 2, wherein said structure 1 is:

and said structure 2 is:

In some embodiments, the gel comprises two or more compounds of structure 1. In some embodiments, the gel comprises two or more compounds of structure 2. In some embodiments, the gel comprises one or more compounds of structure 1 and one or more compounds of structure 2. In some embodiments, the one compound of structure 1 is Tris(2-hydroxyethyl)methylammonium Hydroxide ("THMH"). In some embodiments, the THMH is stabilized with a stabilizing agent. In some embodiments, the electrophoretic separation is capillary electrophoresis. In some embodiments, the capillary electrophoresis is capillary gel electrophoresis. In some embodiments, the capillary electrophoresis is capillary zone electrophoresis. In some embodiments, the one or more compounds of structure 1, or one or more compounds of structure 2, or a mixture of one or more compounds of structure 1 and one or more compounds of structure 2 are present in a concentration between 0.001% wt/wt and 5.0% wt/wt of the gel. In some embodiments, the one or more compounds of structure 1, or one or more compounds of structure 2, or mixture of one or more compounds of structure 1 and one or more compounds of structure 2, are present in a concentration between 0.08% wt/wt and 0.15% wt/wt of the gel.

In another group of embodiments, the invention provides cartridges or capillaries for capillary electrophoretic (CE) separation of analytes of interest, wherein the cartridge or capillary is loaded with a gel, which gel comprises one or more compounds of structure 1, or one or more compounds of structure 2, or a mixture of one or more compounds of structure 1 and one or more compounds of structure 2, wherein said structure 1 is:

and said structure 2 is:

In some embodiments, the gel comprises two or more compounds of structure 1. In some embodiments, the gel comprises two or more compounds of structure 2. In some embodiments, the gel comprises one or more compounds of structure 1 and one or more compounds of structure 2. In some embodiments, the one or more compounds of structure 1 is Tris(2-hydroxyethyl)methylammonium Hydroxide ("THMH"). In some embodiments, the THMH is stabilized with a stabilizing agent. In some embodiments, the gel further comprises polyethylene oxide. In some embodiments, the analyte of interest is a labeled glycan. In some embodiments, the cartridge or capillary is a cartridge. In some embodiments, the cartridge or capillary is a capillary. In some embodiments, the capillary has an interior lumen with walls which are uncoated. In some embodiments, the capillary has an interior lumen with walls which are coated with a coating that (a) does not interfere with CE of said analyte of interest and, (b) prevents resolution of the analyte of interest from degrading over at least 5 runs without conditioning said capillary between each run. In some embodiments, the coating does not interfere with CE of the analyte of interest and prevents resolution of the analyte from degrading over at least 10 runs without conditioning said capillary between each run. In some embodiments, the coating of the walls is polyvinyl alcohol. In some embodiments, the one or more compounds of structure 1, or one or more compounds of structure 2, or mixture of one or more compounds of structure 1 and one or more compounds of structure 2, are present in the gel in a concentration between 0.001% wt/wt and 5.0% wt/wt of the gel. In some embodiments, the one or more compounds of structure 1, or one or more compounds of structure 2, or mixture of one or more compounds of structure 1 and one or more compounds of structure 2 are present in the gel in a concentration between 0.08% wt/wt and 0.15% wt/wt of the gel.

In a further group of embodiments, the invention provides systems for electrophoretic separation of analytes, comprising (a) an apparatus for performing the electrophoretic separation and, (b) a gel in which to perform the electrophoretic separation, the gel comprising one or more compounds of structure 1, or one or more compounds of structure 2, or a mixture of one or more compounds of structure 1 and one or more compounds of structure 2, wherein the structure 1 is:

and said structure 2 is:

In some embodiments, the gel comprises two or more compounds of structure 1. In some embodiments, the gel comprises two or more compounds of structure 2. In some embodiments, the gel comprises one or more compounds of structure 1 and one or more compounds of structure 2. In some embodiments, the one or more compounds of structure 1 is Tris(2-hydroxyethyl)methylammonium hydroxide ("THMH"). In some embodiments, the THMH is stabilized with a stabilizing agent. In some embodiments, the electrophoretic separation is capillary electrophoresis. In some embodiments, the capillary electrophoresis is capillary gel electrophoresis. In some embodiments, the capillary electrophoresis is capillary zone electrophoresis. In some embodiments, the one or more compounds of structure 1, or one or more compounds of structure 2, or mixture of one or more compounds of structure 1 and one or more compounds of structure 2 are present in the gel at a concentration between 0.001% wt/wt and 5.0% wt/wt of the gel. In some embodiments, the one or more compounds of structure 1, or one or more compounds of structure 2, or a mixture of one or more compounds of structure 1 and one or more compounds of structure 2 are present in the gel at a concentration between 0.075% wt/wt and 0.2% wt/wt of the gel.

In yet a further group of embodiments, the invention provides methods for performing electrophoretic separation of labeled analytes, comprising (a) loading said analytes onto a gel, which gel comprises an effective amount of one or more compounds of structure 1, or one or more compounds of structure 2, or a mixture of one or more compounds of structure 1 and one or more compounds of structure 2, wherein said structure 1 is:

and said structure 2 is:

and subjecting the labeled analytes in the gel to an electric potential, thereby performing an electrophoretic separation of the labeled analytes. In some embodiments, the gel comprises two or more compounds of structure 1. In some embodiments, the gel comprises two or more compounds of structure 2. In some embodiments, the gel comprises one or more compounds of structure 1 and one or more compounds of structure 2. In some embodiments, the one or more compounds of structure 1 is Tris(2-hydroxyethyl)methylammonium hydroxide ("THMH"). In some embodiments, the THMH is stabilized with a stabilizing agent. In some embodiments, the electrophoretic separation is capillary electrophoresis. In some embodiments, the capillary electrophoresis is capillary gel electrophoresis. In some embodiments, the capillary electrophoresis is capillary zone electrophoresis. In some embodiments, the labeled analytes are labeled glycans. In some embodiments, the one or more compounds of structure 1, or one or more compounds of structure 2, or mixture of one or more compounds of structure 1 and one or more compounds of structure 2 are present in said gel in a concentration between 0.001% wt/wt and 5.0% wt/wt of the gel. In some embodiments, the one or more compounds of structure 1, or one or more compounds of structure 2, or mixture of one or more compounds of structure 1 and one or more compounds of structure 2 are present in said gels in a concentration between 0.075% wt/wt and 0.15% wt/wt of the gel. In some embodiments, the labeled glycans are labeled with a dye having multiple sulfonic acid moieties. In some embodiments, the labeled glycans are labeled with APTS, ANTS, or InstantQ™.

In still a further group of embodiments, the invention provides kits for performing electrophoretic separations, comprising (a) a container holding a gel, which gel comprises an effective amount of one or more compounds of structure 1, or of one or more compounds of structure 2, or of a mixture of one or more compounds of structure 1 and one or more compounds of structure 2, wherein structure 1 is:

and structure 2 is:

and (b) a buffer. In some embodiments, the gel comprises two or more compounds of structure 1. In some embodiments, the gel comprises two or more compounds of structure 2. In some embodiments, the gel comprises one or more compounds of structure 1 and one or more compounds of structure 2. In some embodiments, the one or more compounds of structure 1 is Tris(2-hydroxyethyl)methylammonium hydroxide ("THMH"). In some embodiments, the THMH is stabilized with a stabilizer. In some embodiments, the container holding said gel is a cartridge or a capillary. In some embodiments, the cartridge or capillary is a cartridge. In some embodiments, the said cartridge or capillary is a capillary. In some embodiments, the capillary has an interior lumen with walls which are uncoated. In some embodiments, the capillary has an interior lumen with walls which are coated. In some embodiments, the coating of the walls of the capillary is of polyvinyl alcohol.

BRIEF DESCRIPTION OF THE DRAWINGS

FIGS. 1a and 1b. FIGS. 1a and 1b are electropherograms comparing the resolution of APTS-labeled glycans released from etanercept, a fusion protein biologic therapeutic. FIG. 1a. FIG. 1b.

FIGS. 2a and 2b. FIGS. 2a and 2b are electropherograms comparing the resolution of glycans released from human IgG and then labeled with InstantQ™ in a capillary coated on its interior with polyvinyl alcohol after the first injection of a sample (FIG. 2a) and after a later injection of the same sample (FIG. 2b). The capillary was loaded before each run with fresh gel, to which 0.1% wt/wt of an exemplar quaternary ammonium compound, THMH, had been added, but the capillary was not conditioned between any of the runs. GU=Glucose units. RFU=Relative fluorescence units. FIG. 2a. FIG. 2b.

DETAILED DESCRIPTION

Determining which analytes are present in a sample is important in a number of situations. For example, determining which carbohydrates (or "glycans"), are attached to a glycoconjugate, such as a glycoprotein is important to understanding the pharmacokinetics, immunogenicity, and potential therapeutic effectiveness of the glycoprotein. Accordingly, it would be desirable to improve the detection of analytes of interest, such as glycans, present in a given sample.

Often, the analytes present in a sample are detected by separating them by electrophoresis and then detecting the separated analytes. As noted in the Background, a number of electrophoretic separation techniques are known in the art. These include, but are not limited to, slab gel, capillary electrophoresis ("CE"), electrofiltration, Differential In-gel Electrophoresis ("DIGE"), zone electrophoresis, Isoelectric Focusing ("IEF"), native electrophoresis, 2-dimensional electrophoresis, immunochemical/immunofixation electrophoresis, immobilized pH gradient electrophoresis, microchips, moving boundary, isotachophoresis, pulse-field electrophoresis, as well as combinations of these. Within capillary electrophoresis, techniques include capillary gel electrophoresis, or "CGE," which separates molecules based on molecular size, and capillary zone electrophoresis, or "CZE," which separates molecules based on charge:mass ratio.

While electrophoretic techniques often give good separation of many analytes, some analytes, and particularly glycans, co-migrate with each other, rendering it difficult to determine which are present and in what quantities. Reducing co-migration of analytes present in a given sample, such as labeled glycans, would improve resolution of the analytes present in the sample. Unfortunately, to date, there have been few if any compositions and methods for reducing the co-migration of analytes, such as labeled glycans, and thus for improving resolution of the analytes.

Surprisingly, we have found that the presence in a gel of a low concentration of Tris(2-hydroxyethyl)methylammonium Hydroxide (CAS No. 33667-48-0: the compound is sometimes referred to herein as "THMH" or as "TEMAH"), a compound previously used primarily for cleaning semiconductors, significantly improves the resolution of analytes labeled with certain labels when the labeled analytes are subjected to electrophoretic separation in the gel. For example, analytes such as glycans labeled with APTS (8-aminopyrene-1,3,6-trisulfonic acid, trisodium salt), CAS name/number: 1,3,6-Pyrenetrisulfonic acid, 8-amino-, trisodium salt 196504-57-1, with an activated form of APTS as taught by U.S. Pat. Nos. 8,124,792 and 8,445,292, or with other labels with multiple sulfonic acid moieties, can be better resolved by CGE when small amounts of THMH are present in the gel during the electrophoresis. In studies underlying the present invention, the presence of THMH in the gel broadened out the separation and improved the resolution of the analytes in the CGE separation. Some studies underlying the present invention tested the effect of THMH on the separation of Man5 (also sometimes referred to herein as "Man-5" or "Man-5 glycan"), a glycan that can be particularly hard to resolve in CGE separations, using APTS, which does not give adequate separation of Man5 in gels by itself. Studies revealed that THMH helped to maintain the peak shape of Man5 during the gel separations, and, moreover, it did so over an number of runs. As practitioners will appreciate, maintaining peak shape in separations of analytes is desirable as it helps keep the peaks of closely co-migrating analytes from overlapping, which can happen if the peaks broaden during the procedure Given that all electrophoretic techniques rely on the movement of the analyte through a gel under the influence of an electric field, it is believed that the results obtained in the studies using a CGE system will also obtain with other forms of electrophoresis using gels, and especially embodiments in which the electrophoretic separation is conducted in a microfluidic environment. Further, since the movement of the compound of interest through the gel under the influence of an electric field is a feature of electrophoretic techniques regardless of the type of compound being analyzed, it is believed that, while increasing resolution of glycans is a preferred embodiment, use of THMH and other compounds discussed herein will also increase the resolution of other labeled carbohydrates and compounds containing them.

THMH is a preferred embodiment of a quaternary ammonium compound for use in some embodiments. It is believed, however, that similar results in improving resolution of analytes in electrophoresis separations will be obtained using other quaternary ammonium compounds containing a methyl and three terminal hydroxyl groups, in which the methyl group is attached to the nitrogen not directly, as in THMH, but through an alkyl linker of 1 to 5 carbons. Accordingly, in these embodiments, the trihydroxyl quaternary ammonium compound has the structure shown in Structure 1.

Structure 1

Compounds of Structure 1 will sometimes be referred to herein as "trihydroxyl quaternary ammonium compounds."

It is further believed that similar results in improving resolution of analytes in electrophoresis separations will be obtained using tetrahydroxyl quaternary ammonium compounds in which the methyl of THMH is instead a fourth hydroxyl group, which may be attached to the nitrogen directly or through an alkyl linker of 1 to 5 carbons. In these embodiments, therefore, the tetrahydroxyl quaternary ammonium compound has the structure shown in Structure 2.

Structure 2

Compounds of Structure 2 will sometimes be referred to herein as "tetrahydroxyl quaternary ammonium compounds." In a preferred embodiment, the hydroxyl group of the compound of structure 2 is bonded directly to the nitrogen. In some embodiments, the compound of structure 2 has 1 carbon between the hydroxyl group and the nitrogen. In some embodiments, the compound of structure 2 has 2 carbons between the hydroxyl group and the nitrogen. In some preferred embodiments, the compound of structure 2 has 3 carbons between the hydroxyl group and the nitrogen. In some preferred embodiments, the compound of structure 2 has 4 carbons between the hydroxyl group and the nitrogen. In some preferred embodiments, the compound of structure 2 has 5 carbons between the hydroxyl group and the nitrogen.

The inventive compositions and methods are particularly suited for electrophoresis separations using a gel for size separation of analytes, including hybrid techniques. In some embodiments, the electrophoretic separation using a gel is capillary electrophoresis. In some embodiments, the capillary electrophoresis is capillary gel electrophoresis.

The trihydroxyl quaternary ammonium compounds or tetrahydroxyl quaternary ammonium compounds discussed above can be used individually, or as a mixture of both a trihydroxyl quaternary ammonium compound or tetrahydroxyl quaternary ammonium compound, or of two trihydroxyl quaternary ammonium compounds or of two tetrahydroxyl quaternary ammonium compounds. Any particular trihydroxyl quaternary ammonium compound, tetrahydroxyl quaternary ammonium compound, or mixture thereof, can be readily tested to determine whether it improves resolution of the analyte or analytes of interest by introducing samples of the analytes or analytes to separation in a first gel, gel 1, made with the compound or mixture of compounds being tested and duplicate samples into a second gel, gel 2, which does not have the test compound or compounds, and determining if resolution of the analyte of choice is (a) improved, (b) the same, or (c) worse when the test sample is separated in gel 1 compared to when the test sample is separated in gel 2. For example, if the analytes of interest are the glycans Man5, A1F and G0F-N, labeled with, for example, ANTS, APTS, or InstantQ™ (ProZyme, Inc., Hayward, Calif.), they can be subjected to CGE in a first gel containing a test amount of the test compound or mixture to see if the different labeled glycans of interest are better separated from one another than when separated by CGE in a second gel whose only difference from the first gel is the absence of the test compound or mixture.

Typically, the compound or mixture is conveniently introduced into the gel composition as a solution, but it can be mixed as a powder into the buffer used to form the gel matrix, or introduced by other convenient means known in the art. Solutions of the trihydroxyl quaternary ammonium compound or tetrahydroxyl quaternary ammonium compound may further comprise a small amount of an antibacterial agent. THMH, for example, is commercially available from TCI America (Portland Oreg.) at a concentration of 40-50% in water, stabilized with the agent MEHQ (4-Methoxyphenol, CAS Number 150-76-5). It is believed that the good results achieved in studies underlying the present disclosure conducted with THMH are due to the presence of the THMH and not to the small amount of MEHQ present in the THMH used in the studies.

Recipes for making gels for use in different electrophoresis applications are well known in the art. It is expected that persons of skill in the art will be familiar with recipes suitable for the particular electrophoretic technique to be used for analysis of the analyte or analytes of interest. In some preferred embodiments, the gel recipes are for gels for use in capillary electrophoresis. In some preferred embodiments, the gel recipes are for gels for use in capillary gel electrophoresis. The trihydroxyl quaternary ammonium compound or tetrahydroxyl quaternary ammonium compound, or a mixture of both a trihydroxyl quaternary ammonium compound or tetrahydroxyl quaternary ammonium compound or of two or more trihydroxyl quaternary ammonium compounds or of two or more tetrahydroxyl quaternary ammonium compounds is preferably added to the gel recipe of choice in amounts of 0.005% to 5%, 0.0075% to 4%, 0.01% to 3%, 0.025% to 2%, 0.025% to 1%, 0.05% to 0.75%, 0.05% to 0.60%, 0.075% to 0.50%, 0.075% to 0.4%, 0.075% to 0.3%, 0.075% to 0.2%, 0.075% to 0.15%, 0.08% to 0.125%, 0.85% to 0.125%, 0.09% to 0.120%, 0.09% to 0.115%, 0.09% to 0.11%, and 0.1%. The percentage 0.1% was found to be the best for separating Man5 from other, closely co-migrating glycans. It is expected that the percentages of the quaternary ammonium compound or compounds that work best in separations of a different glycan of interest might be different from the one found to be for separating Man5 from other glycans, but to be within the percentages stated above, and that percentages or concentrations that work best for any particular glycan or other labeled carbohydrate can be readily determined using the assays taught in this disclosure. The percentages can be calculated on wt/wt basis or on v/v basis. The two calculations are very similar, but there might be a slight difference in the optimal concentration of the compound depending on which calculation is used. In studies in the course of the present work, mixtures were made using both calculations and no functional difference was seen.

The small amounts of the THMH or other trihydroxyl quaternary ammonium compound or tetrahydroxyl quaternary ammonium compound or mixtures of these to be added to the recipe for making the electrophoresis gel can be hard to pipette or otherwise manipulate for introduction into the gel recipe. The solution comprising the THMH or other trihydroxyl quaternary ammonium compound or tetrahydroxyl quaternary ammonium compound is therefore sometimes first diluted by two- to ten-fold to bring up the amount of the solution containing the compound to be introduced. For example, the THMH stock solution (45-50% w/w) can be diluted 10-fold for a working concentration of ~5% with water containing MEHQ. This working concentration of THMH is then added to a gel mixture to form a gel with a final concentration of 0.05-0.5% THMH in the gel. In some embodiments, it is desirable to increase the accuracy of the final solution by avoiding the need for intermediate solutions. In these embodiments, the THMH or other trihydroxyl quaternary ammonium compound or tetrahydroxyl quaternary ammonium compound or mixtures of these to be added to the recipe ("additive") can be weighed out, the weight of the gel solution needed to dilute the additive to the desired concentration calculated, the additive placed in a container suitable to hold the gel in the amount to be used to dilute the additive, and the gel solution added directly to the additive in the container. Preferably, the gel solution and additive are then mixed by a technique used in laboratories to mix viscous solutions, for example, by placing the container on a rotating platform or by using a magnetic stirrer.

Any particular concentration of the trihydroxyl quaternary ammonium compound, tetrahydroxyl quaternary ammonium compound, or mixture thereof, present in the resulting gel can be readily tested to see if it causes the current in the electrophoresis apparatus to go above the amount recommended for use, in which case that particular concentration of that particular trihydroxyl quaternary ammonium compound, tetrahydroxyl quaternary ammonium compound, or mixture thereof, is not preferred. The trihydroxyl quaternary ammonium compound, tetrahydroxyl quaternary ammonium compound, or mixture of the same is preferably added to the other components of the gel recipe of choice and stirred to obtain uniform distribution of the trihydroxyl quaternary ammonium compound, tetrahydroxyl quaternary ammonium compound, or mixture of the same in the gel.

Similarly, any particular concentration of any particular trihydroxyl quaternary ammonium compound, tetrahydroxyl quaternary ammonium compound, or mixture thereof, can be readily tested for its effect in improving resolution of the analyte or analytes of interest by subjecting test samples of the analytes to separation in a first gel, gel 1, made with the test concentration of the compound or compounds and in a second gel, gel 2, which does not have the test compound or compounds and determining if resolution of the analyte of choice is improved, the same, or worse when the test sample is separated in gel 1 compared to when the test sample is separated in gel 2. For example, if the analytes of interest are the glycans known in the art as Man5, A1F and G0, labeled with, for example, ANTS, APTS, or InstantQ™ (ProZyme, Inc., Hayward, Calif.), they can be subjected to CGE with the test amount of the test compound or mixture to see if the gel succeeds in separating the different labeled glycans of interest from one another. Analytes labeled by labels other than ANTS, APTS or InstantQ™ can likewise be used to determine whether a particular amount of a particular trihydroxyl quaternary ammonium compound, tetrahydroxyl quaternary ammonium compound, or mixture thereof succeeds in improving resolution of a particular analyte compared to a like separation performed in the absence of the trihydroxyl quaternary ammonium compound, tetrahydroxyl quaternary ammonium compound, or mixture thereof. Amounts of a particular trihydroxyl quaternary ammonium compound, tetrahydroxyl quaternary ammonium compound, or mixture thereof that improve resolution of an analyte of choice in a given gel recipe, but do not result in overheating the apparatus used to conduct the electrophoretic separation are considered to be an effective amount of the trihydroxyl quaternary ammonium compound, tetrahydroxyl quaternary ammonium compound, or mixture thereof.

Definitions

As used herein, the phrases "gel," "gel matrix," and "sieving matrix" are synonyms.

In the context of performing electrophoretic separations, such as by CGE or a hybrid CE procedure using a gel, the term "resolution" refers to the ability to distinguish between two analytes that would otherwise migrate together in the analytical system being used to separate them. For convenience of reference, the term "CGE" as used herein includes hybrid CE procedures using a gel unless otherwise required by context The term "label," with regard to labeling an analyte of interest, means chemically attaching to that analyte of interest a fluorescent moiety or a UV-visible dye.

The phrase "analyte has been labeled by being reacted with" a named compound means that the label attached to a labeled analyte is the label that remains after an analyte has been contacted with the named compound under conditions allowing it to label the analyte with a fluorescent moiety or with a UV-visible dye.

Man5

Mammalian antibodies and fusion proteins are important, and very expensive, groups of therapeutics, and are typically produced in commercial fermentation systems. Monitoring of the levels of the glycan known as "Man5" (Mannopentaose-di-(N-acetyl-D-glucosamine), or "Oligomannose-5 glycan," CAS No. 66091-47-2, also known as "Man-5" or "Man-5 glycan"), during production of the antibody or fusion protein can serve as a marker that the fermentation system is under stress and allow intervention, hopefully in time to save the production lot. The following structure for Man-5 glycan is taken from the Sigma-Aldrich website (Sigma-Aldrich, St. Louis, Mo.):

CE and CGE

Capillary electrophoresis and CGE have been used to separate various analytes for over two decades. It is therefore expected that practitioners are familiar with the various protocols and reagents used in the art for performing CGE and hybrid CE methods using gels, and that these protocols and reagents need not be discussed at length here. For example, CE in general, and CGE in particular, are discussed in detail in texts such as "Capillary Electrophoresis Methods for Pharmaceutical Analysis," Volume 9, Ahuja and Jimidar, eds., Elsevier, London (2008), "Capillary Electrophoresis Guidebook: Principles, Operation, and Applications," (Methods in Molecular Biology), Altria, ed., Humana Press, Totowa, N.J. (2010), and "Capillary Electrophoresis: Methods and Potentials," Engelhardt et al., eds., Friedr, Vieweg & Sohn, Braunschweig/Wiesbaden (1996). CE of carbohydrates in particular is also taught in a number of texts, including "Capillary Electrophoresis of Carbohydrates" (Methods in Molecular Biology, Vol. 213), Thibault and Honda, eds., Humana Press Inc., Totowa, N.J. (2003), "Capillary Electrophoresis of Carbohydrates: From Monosaccharides to Complex Polysaccharides," Volpi, ed., Humana Press, Totowa, N.J. (2011) and "Carbohydrate Analysis: High Performance Liquid Chromatography and Capillary Electrophoresis," El Rassi, ed., Elsevier Science B.V., Amsterdam, the Netherland (1995). Chapter 8 of this last reference discusses the use of a variety of CE techniques, including both CZE and CGE, for the analysis of carbohydrates and glycoconjugates.

Gels, Cartridges, Capillaries, and Labels

Gels for electrophoretic separation of various analytes are well known in the art and contain different compositions adjusted for the properties of the analyte of interest in the particular electrophoretic technique chosen by the practitioner. It is expected that the person of skill is familiar with the various gels used in the art to subject particular analytes of interest to electrophoretic separation by a selected electrophoretic separation technique, including gels and techniques for glycans and other compounds containing carbohydrates.

In some embodiments for separations of glycans, the gels used in the inventive methods and compositions, particularly for CGE separation, are as taught in U.S. Pat. No. 8,163,152 (the "'152 Patent"), at col. 12, lines 15-23. In some preferred embodiments, the gel is made following the recipe set forth in the '152 patent at col. 12, lines 25-35, with the following modifications: (1) the polyethylene oxide ("PEO") of 7000000 mwt g/mol set forth in the recipe was replaced by PEO of 8000000 mwt g/mol, as PEO of 7000000 molecular weight is currently not commercially available, and (2) the EtBr is omitted (this modified recipe is sometimes referred to herein as the "modified PEO gel"). In some embodiments, the mwt g/mol of the larger and the smaller PEOs set forth in the recipe can independently be ±20% of the mwt g/mol values stated. And, regardless of the size of the PEOs used, EtBr is preferably omitted from the gel. The entirety of the '152 Patent is incorporated by reference, and the portions cited above are specifically incorporated by reference. As persons of skill are aware, "PEO" and "polyethylene glycol," or "PEG," are chemically synonymous, but "PEG" is typically used to refer to polymers below 20,000 g/mol, while "PEO" is typically used to refer to polymers above that point.

In some embodiments in which the analyte of interest is a glycan, the gel may be composed of a compound other than PEO used for capillary gel electrophoresis of glycans, such as hydroxypropylmethylcellulose (HPMC). While PEO is a particularly preferred gel, other neutral hydrophilic polymers, such as alkyl celluloses, polyvinyl alcohol, dextrans, or polyacrylamide, may be used.

Gel used for electrophoretic separations may be created by any means known in the art. The compounds of structure 1, structure 2, or mixtures thereof, are conveniently added to the reagents before the gel is formed to allow even distribution of the compounds of structure 1, structure 2, or mixtures thereof, within the gel. In many instruments, the gel is disposed in one or more containers, the end of a capillary is introduced into the gel, and the gel is driven into the capillary, typically by air pressure.

In some embodiments, the gel may be disposed in a cartridge and driven into a capillary fluidly connected to the cartridge, facilitating changes of gel in the capillary between analyses of samples. The cartridges are typically designed for use in an analytical instrument configured to accept them, such as the gel cartridges configured for use with a GL1000 glycan analyzer (BiOptic Inc., New Taipei City, Taiwan (R.O.C)), and preferably allow quick changes of gels, expediting a series of analyses. Typically, the gel is made in bulk, dispensed into cartridges, and cartridges already filled with the gel of choice are then purchased by the practitioner intending to use the cartridge to perform CGE separations in an instrument configured to receive the cartridge.

For analysis of glycans, suitable labels include APTS and InstantQ™ (ProZyme, Inc., Hayward, Calif.). ANTS (typically purchased as 8-Aminonaphthalene-1,3,6-trisulfonic acid disodium salt, the sodium salt hydrate, CAS No. 5398-34-5), and other polysulfonate labels for glycans can also be used. It is believed that the compounds of structure 1, structure 2, or mixtures thereof, are particularly useful in electrophoretic separations in which the label used to label the analyte of interest comprises a plurality of sulfonic acid moieties.

Separation of Man-5 Glycan from Other Glycans

As noted in a preceding section, changes in the level of Man5 in a fermenter can signal stress in the fermentation reaction which could result in loss of an entire production run of a valuable therapeutic agent, such as one of the antibodies approved by the FDA as an anti-cancer therapeutic. Accordingly, it has become important to determine the amount of Man5 present in the system. Unfortunately, monitoring the amount of Man5 by CGE has been difficult because other glycans can be present that co-migrate with Man5 using conventional CGE gels. When the glycans are labeled with APTS, the glycans that co-migrate with Man5 are A1F, G0, and G0F-N. When the glycans are labeled with InstantQ™, the glycans that co-migrate with MAN-glycan are G0F-N and A1F. As reported in a previous section, studies underlying the present disclosure showed that the exemplar quaternary ammonium compound THMH improved the resolution of Man-5 glycan from other, closely co-migrating glycans when the Man-5 glycan was labeled with APTS. In particular, the peak shape of APTS-labeled Man-5 glycan was maintained during the separation, making it easier to distinguish the Man-5 glycan from G0F-N, G0, and A1F.

Uncoated and Coated Capillaries

As noted above, studies underlying the present disclosure found that the presence of the exemplar quaternary ammonium compound THMH during capillary electrophoresis caused a marked improvement in the resolution of some hard-to-resolve glycans. Thus, the presence of a quaternary ammonium compound in a CE separation of an analyte is advantageous and can be used to improve the ability to analyze a sample for the presence of analytes of interest that would otherwise be difficult to distinguish from other analytes co-migrating with the analyte or analytes of interest. In some preferred embodiments, the quaternary ammonium compound is THMH. In some preferred embodiments, the analytes are glycans and the gels used are suitable for use in analyzing glycans.

Most current CE instruments are designed to wash the capillary between each run of sample and to introduce fresh gel into the capillary. Such washes are referred to as "regenerating" or "conditioning" the capillary, and are used in many CE protocols to improve reproducibility. D. Heiger, HIGH PERFORMANCE CAPILLARY ELECTROPHORESIS, AN INTRODUCTION (Agilent Technologies, Publication 5968-9963E, Germany, 2000) ("Heiger"), p. 92, for example, states that capillaries can be conditioned by washing them with a strong base, with a strong acid, with an organic compound such as methanol or DMSO, or with a detergent, and following the wash by a rinse.

While washing capillaries between each run to condition them does maintain their resolution, it also adds considerable time when multiple analyses have to be performed. The steps to wash, rinse, and refill the capillary with fresh gel are time consuming and can double or more the time required for analyses to be completed. It would be desirable to remove or reduce the time needed to perform multiple runs by reducing the need to condition capillaries between each run.

ProZyme's Gly-Q™ Glycan Analysis System provides reproducible results without the need to condition the capillary between each run. When the exemplar quaternary ammonium compound THMH was added to the gel used in the system, it was found to significantly improve the ability to resolve labeled Man5 from other labeled glycans in the sample that would otherwise co-migrate with it. That ability, however, degraded after a number of runs had been made. Typically, 20-50 runs could be made before the peaks representing the labeled glycans broadened and could overlap, reducing the ability to resolve the labeled Man5 from other labeled glycans in the sample that closely co-migrated with it.

In studies underlying the present disclosure, washing the capillary with a solution with an acid (in the studies, acetic acid) or a solution with a low pH ((in the studies, 0.1M MES, 2-(N-morpholino)ethanesulfonic acid, with a pH of 3.5), followed by a water rinse and fresh gel containing an exemplar quaternary ammonium compound, maintained the ability of the capillary to provide excellent resolution of the glycans used as exemplar analytes. Without wishing to be bound by theory, it is believed that the reduced resolution after multiple separations in the same capillary without conditioning may be caused by an interaction between the amines of the quaternary ammonium compound and the walls of the capillary and that this interaction is eliminated when the capillary is conditioned. It is expected that the same results will obtain when other conventional reagents for conditioning capillaries are used. Thus, the inventive compositions and methods are compatible for use with instruments that wash capillaries between each run, using standard protocols for conditioning capillaries.

While the washing of the capillaries allowed the use of THMH to improve the resolution of Man5 from other closely-migrating glycans, it decreased the ability to use the Gly-Q™ Glycan Analysis System to reduce the overall time for glycan analysis by eliminating the time needed to condition the capillaries used for the analyses. To reduce the need to condition the capillaries when THMH is present in the gel, another approach was employed.

The studies reported in the preceding paragraphs in this section were performed using capillaries that were not coated on their interior. (As practitioners will appreciate, most if not all capillaries are coated on their exterior to reduce their brittleness.) Capillaries coated on their interior with any of a number of coatings are commercially available and are typically present to prevent interactions of an analyte with the wall. We are not aware of a coating being used to improve the performance of a gel additive, such as a quaternary ammonium compound.

In studies underlying the present disclosure, commercially-available capillaries coated with permanently-attached coatings were modified to fit the system and tested to see if the presence of the coating affected the resolution of analytes when the exemplar quaternary ammonium compound THMH was present in the gel, using glycans as the exemplar analytes and the difficult-to-resolve glycan Man5 as the glycan whose resolution from other, closely migrating glycans, was desired. All of the capillaries tested were obtained from Agilent Technologies, Inc. (Santa Clara, Calif.). The names of the coatings discussed below are as those coatings are referred to by Agilent on its website.

Five different types of coated capillaries were tested: capillaries coated with polyvinyl alcohol, or "PVA," with μSIL-WAX, with DB-1, with μSIL-DNA, or with CEP. Agilent's website describes the μSIL-WAX coating as "a modified, polyethylene oxide, hydrophilic coating." DB-1 is described as being of dimethylpolysiloxane. Agilent's website describes μSIL-DNA as a proprietary fluorocarbon polymer, and describes CEP as a permanently bonded polymer coating which shields the silanol functionality of the capillary surface and helps prevent sample adsorption.

As shown in Example 3, below, capillaries coated with polyvinyl alcohol, or "PVA," showed no interference with glycan resolution when THMH was present, and no degradation in the ability to resolve Man5 from other glycans when multiple runs of samples and standards were run without conditioning between the runs. Two of the other types of coated capillaries tested, capillaries coated with μSIL-WAX or with DB-1, were found not to degrade the ability of the THMH-gel to resolve Man5 from other closely migrating glycans. While they were not tested over multiple runs as of the present disclosure, either of these coatings could be used at least for single run applications (for example, with CE instruments which wash the capillary and replace the gel between each run, as discussed above), and may also be suitable for multiple-use applications.

The two final types of coated capillaries tested, μSIL-DNA and "CEP," were found to destroy resolution of glycans as exemplar analytes. Accordingly, capillaries coated with μSIL-DNA or CEP are not preferred for use when the analytes of interest are glycans.

The ability to perform over multiple runs of analytes in the same capillary without degradation of resolution in PVA-coated capillaries, or capillaries coated on their interior with other coatings that protect against degradation and which do not themselves interfere with CE of the analytes, allows the conditioning steps to be avoided over a number of runs. This allows the time to conduct the analysis of the analytes to be reduced by at least half, and provides a significant advantage over current instruments and protocols that rely on reconditioning the capillary between each run to improve reproducibility.

Capillaries coated on their interior with any particular coating other than the ones tested in the studies underlying the present disclosure can be readily tested to determine if the coating protects against degradation in resolution of any particular quaternary ammonium compound or mixture of such compounds, and does not itself interfere with CE of an analyte of interest. For example, two capillaries, one coated with a coating of interest and the other uncoated, can be filled with an identical gel comprising the particular quaternary ammonium compound or mixture thereof in question, be injected with the analyte of interest labeled with a detectable label (for example, Man5 labeled with APTS) in combination with other analytes, also labeled with a detectable label, expected to closely co-migrate with the analyte of interest (for example, G0F-N and A1F), be subjected to electrophoresis, thereby performing a run, and determining, (a) whether the presence of the coating had a detrimental effect on the ability to resolve the presence of the analyte of interest from the other analytes present expected to co-migrate with it compared with the resolution of the analyte in the uncoated capillary, over the first run and, if it does not, second, (b) performing a plurality of such runs without conditioning the capillary between each run, and analyzing whether the coating prevents degradation of resolution over a desired number of runs, such as 5 runs, 10 runs, 15 runs, 20 runs, 50 runs, 75 runs, 100 runs, 150 runs, or 200 runs, with coatings that prevent degradation of resolution over more runs being more preferred than coatings that prevent degradation only over a smaller number of runs. As noted above, PVA-coated capillaries did not show a degradation in resolution over more than 200 runs when tested in a capillary that was not conditioned between runs, and are particularly preferred.

Kits

In some embodiments, the inventive gels can be provided in kits for performing capillary electrophoresis. The kits may comprise a container holding a gel suitable for performing CE comprising a compound of structure 1, a compound of structure 2, or a mixture of one or more compounds of structure 1 and of structure 2, and a container holding a buffer suitable for use in performing CE. In preferred embodiments, the compound or compounds of structure 1, structure 2, or both, are present in a concentration (or combined concentration, if more than one such compound is present) of 0.05% wt/wt to 0.5% wt/wt, with 0.075% wt/wt to 0.150% wt/wt being more preferred. Suitable buffers, such as MES, are well known in the art. In some embodiments, the container holding the gel may be a cartridge configured to introduce the gel into one or more capillaries, or may be a capillary or a plurality of capillaries. The one or more capillaries may be coated on their interior with a coating that does not interfere with CE of the analytes of interest and is preferably a coating that prevents the improvement in resolution of the analytes from degrading over a number of runs, such as 50, 100, 200. In some preferred embodiments, the coating may be polyvinyl alcohol.

EXAMPLES

Example 1

This Example sets forth the protocols used in CE separations of glycan samples in the studies set forth in the Figures. The trademarked reagents and instruments listed in the protocol are products of ProZyme, Inc. (Hayward, Calif.).

All samples were labeled with APTS or with InstantQ™, using commercially available kits. Experiments were performed on the Gly-Q™ Glycan Analysis System using the following:

a. Separation Capillaries—one of these three were used in each experiment:
  i. Gly-Q™ G1 Cartridge (standard gel, using an uncoated capillary);
  ii. Gly-Q™ G1 Cartridge (same gel as in (i), but with THMH added at 0.1% wt/wt, using an uncoated capillary); or
  iii. Gly-Q™ G1 Cartridge (same gel as (i) but with THMH added, using a PVA-coated capillary).
b. Separation Buffer: Gly-Q™ Separation Buffer
c. Calibration Standard: Gly-Q™ GU Ladder
d. Calibration Standard Injection: 2 kV for 2 seconds
e. Migration Standard: Gly-Q™ Migration Standards (upper and lower)
f. Migration Standard Injection: 2 kV for 2 seconds
g. Sample Injection: 2 kV for 2 seconds
h. Separation: 10 kV for 120 seconds Data analysis was performed using Gly-Q™ Manager software. Results are presented using Glucose Unit (GU) values.

For calibration purposes, all analyses started with an injection ("Injection 1") of the calibration standard. Thus, in all studies, "Injection 2" was the first injection and analysis of the sample of interest.

Example 2

This Example presents the results of a study comparing the resolution of Man5 from the closely co-migrating glycans A1F and G0F-N when the gel normally sold with the Gly-Q™ G1 Cartridge is used, and when 0.1% of an exemplar quaternary ammonium compound, THMH, is added to the gel.

Figure 1A:
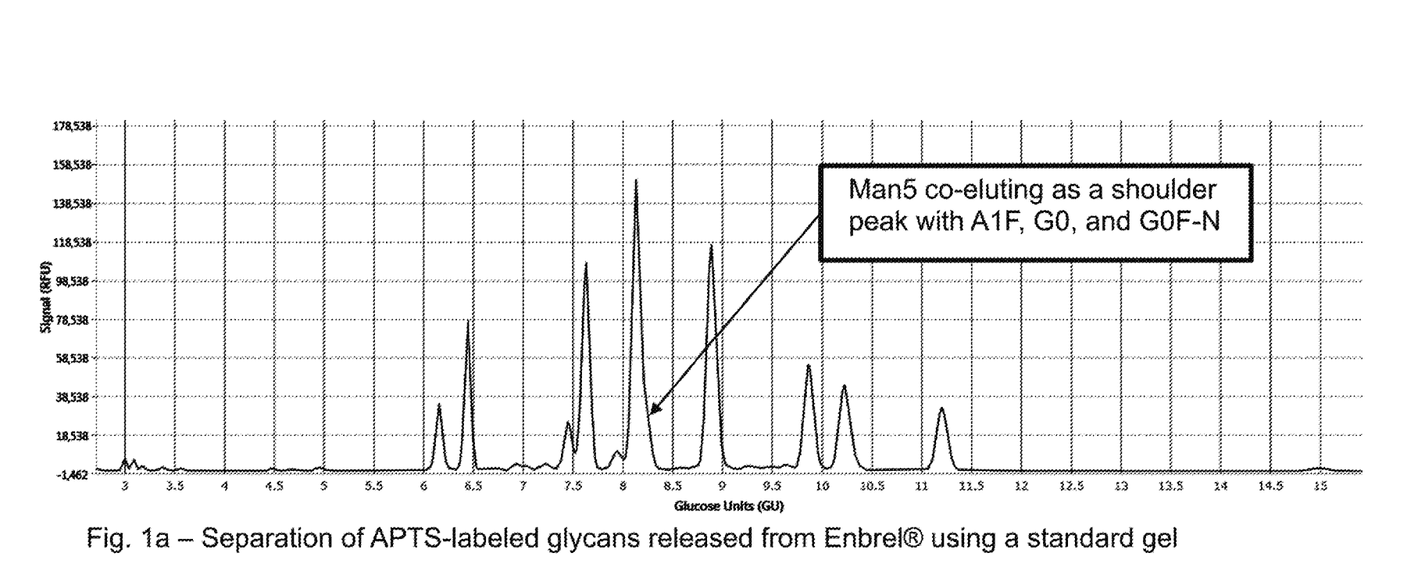
FIG. 1a is an electropherogram show the resolution of the APTS-labeled glycans using a standard gel. An arrow points to a peak in which the separation has failed to resolve Man5 from APTS-labeled A1F, G0, and G0F-N, other glycans that closely co-migrate with Man5.
Figure 1B:
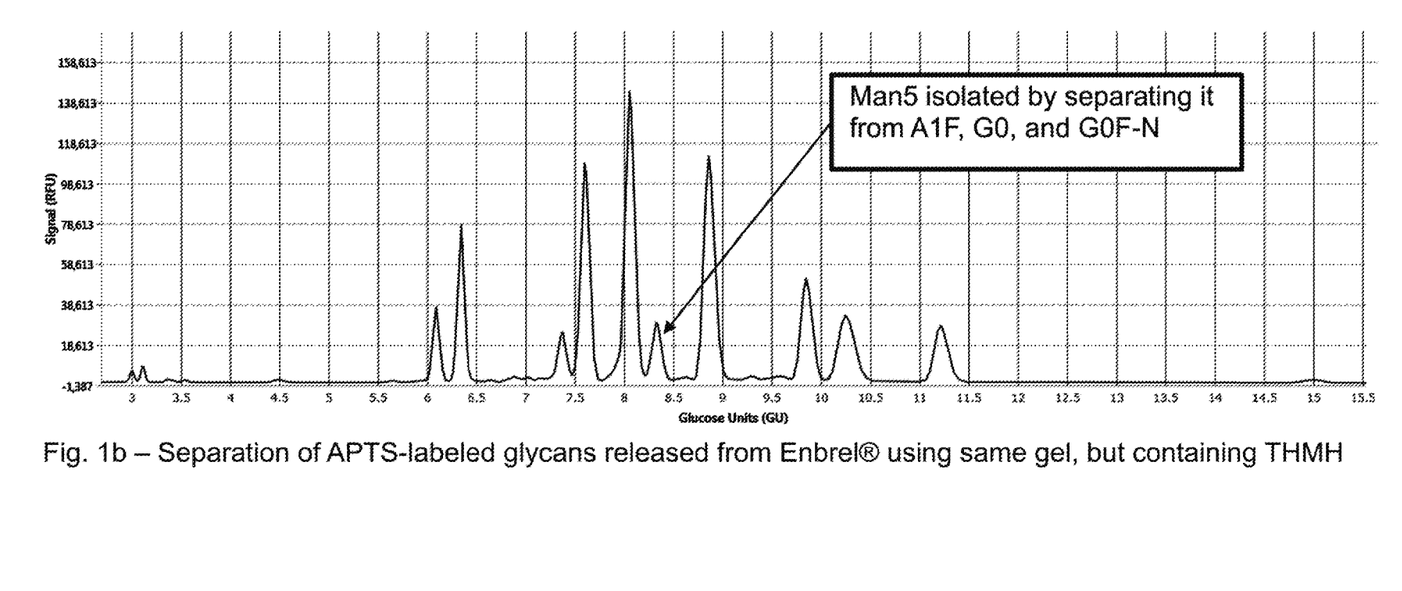
FIG. 1b is an electropherogram shows the resolution of the APTS-labeled glycans separated using the same reagents, but in which the gel further comprises 0.1% of the exemplar quaternary ammonium compound, THMH. As shown by the arrow, in FIG. 1B, the peak for the APTS-labeled Man5 is separated from the peak for A1F, G0, and G0F-N. GU=Glucose units. RFU=Relative fluorescence units.

Enbrel®, or etanercept, is a fusion protein biologic that inhibits tumor-necrosis factor that is approved for use in the U.S. against several forms of arthritis. Glycans were released from etanercept by enzymatic digestion, labeled with APTS, and subjected to CE. FIG. 1a is an electropherogram showing the separation of the released, labeled glycans on the gel sold with the Gly-Q™ G1 Cartridge. An arrow points to a peak comprising Man5, A1F and G0F-N, two other glycans that closely co-migrate with Man5. Thus, CE in this gel did not result in separation of Man5 from other, closely co-migrating glycans. FIG. 1b is an electropherogram showing the resolution of the same APTS-labeled glycans on the same platform with the same reagents, but in which the gel further comprises 0.1% of the exemplar quaternary ammonium compound, THMH. As shown by the arrow in FIG. 1B, the peak for the APTS-labeled Man5 separated from the peak for A1F and G0F-N.

Example 3

This Example presents two electropherograms comparing the resolution of glycans released from human IgG by enzymatic digestion, labeled with the dye InstantQ™, and subjected to CE in a capillary coated on its interior with polyvinyl alcohol.

Figure 2A:
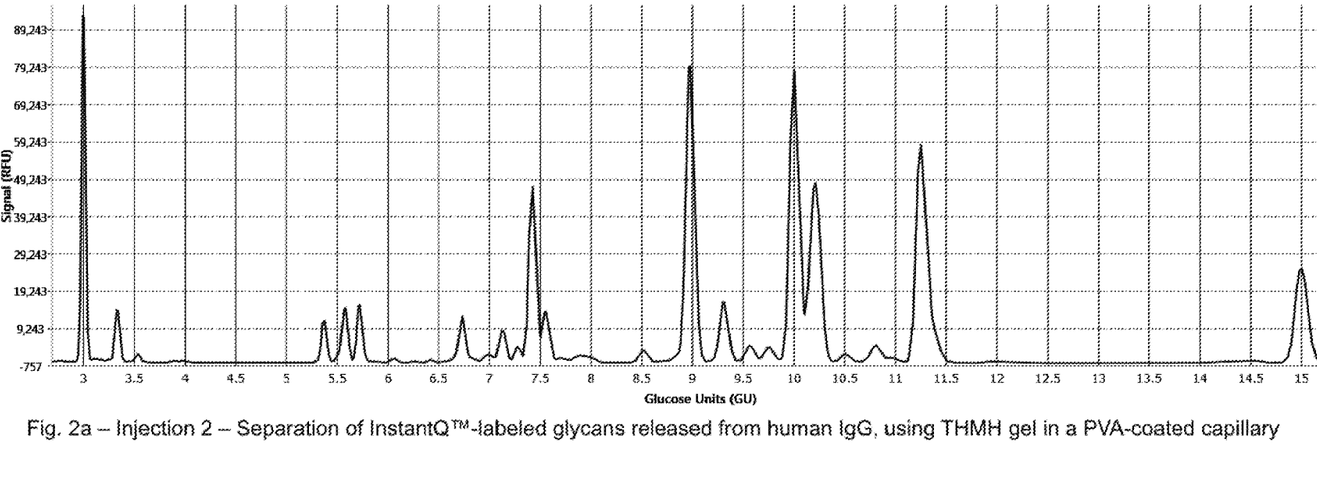
FIG. 2a is an electropherogram showing the separation of InstantQ™-labeled glycans released from human IgG in the first run of the glycans (as injection 1 was of a ladder of standards, the injection is labeled "Injection 2").

FIG. 2a is an electropherogram showing the separation of InstantQ™-labeled glycans released from human IgG in the first injection of sample into a PVA-coated capillary loaded with a standard gel to which 0.1% wt/wt of an exemplar quaternary ammonium compound, THMH, has been added (since the first injection was of the ladder of standards, this injection is labeled "Injection 2").

Figure 2B:
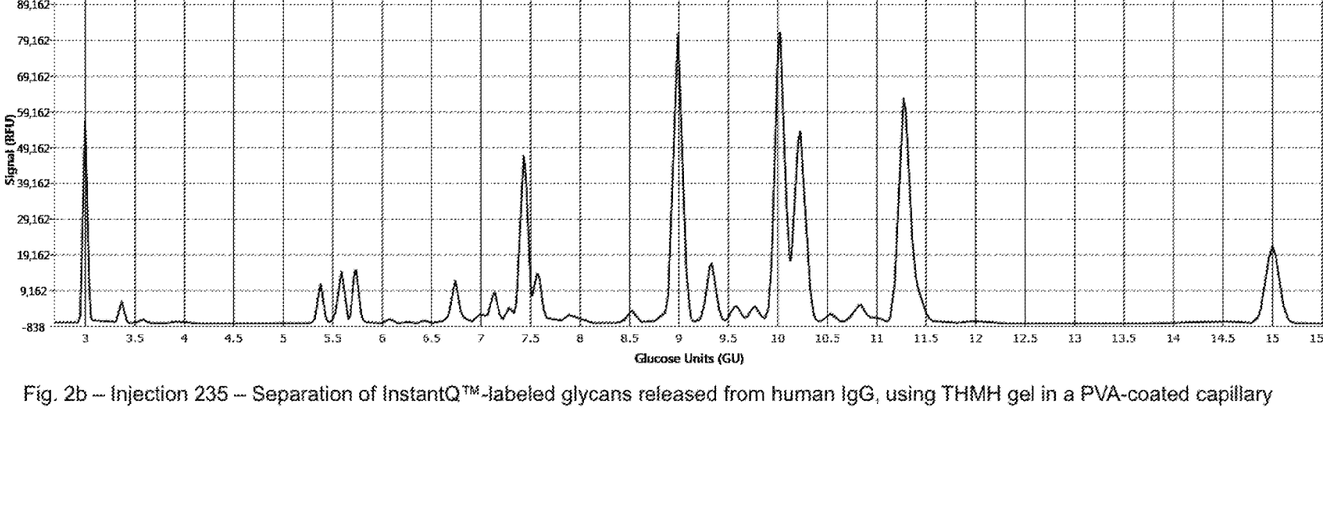
FIG. 2b is an electropherogram showing the separation of InstantQ™-labeled glycans released from human IgG after 234 more separations in the same PVA-coated capillary (as noted, since the first injection was of a ladder of standards, this is "Injection 235"). The capillary was loaded with fresh gel between runs, but was not conditioned between the run presented in FIG. 2a and the one presented in FIG. 2b.

FIG. 2b is an electropherogram showing the separation of the same sample of InstantQ™-labeled glycans released from human IgG after 234 more separations over four days in the same PVA-coated capillary (as noted, since the first injection was of the ladder of standards, this injection is labeled "Injection 235"), including separations of glycans labeled with a different label and of additional ladders of standards. The capillary had fresh gel loaded into it after each injection and electrophoresis, but was not conditioned between any of the 234 runs between the one presented in FIG. 2a and the one presented in FIG. 2b. A comparison of FIGS. 2a and 2b reveals that, while the height of some peaks has changed, the peaks for each component remained clearly identifiable in both electropherograms. Accordingly, use of a PVA-coating in the capillary provided excellent reproducibility of glycan separations with a gel comprising an exemplar quaternary ammonium compound, without the need to condition the capillary between each separation, and without the time that would have been required to condition the capillary more than 200 times between the two separations.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A gel for electrophoretic separation of analytes, said gel comprising
   (a) two or more compounds of structure 1,
   (b) a mixture of one or more compounds of structure 1 and of one or more compounds of structure 2, or
   (c) one or more compounds of structure 2,
   wherein said structure 1 is:

and said structure 2 is:

2. The gel of claim 1, wherein said gel comprises two or more compounds of structure 1.

3. The gel of claim 1, wherein said gel comprises one or more compounds of structure 1 and one or more compounds of structure 2.

4. The gel of claim 1, wherein said gel comprises one or more compounds of structure 2.

5. The gel of claim 1, wherein said gel further comprises polyethylene oxide.

6. A cartridge or capillary for capillary electrophoretic (CE) separation of analytes of interest, wherein said cartridge or capillary is loaded with a gel, which gel comprises
   (a) two or more compounds of structure 1,
   (b) a mixture of one or more compounds of structure 1 and of one or more compounds of structure 2, or
   (c) one or more compounds of structure 2,
   wherein said structure 1 is:

and said structure 2 is:

7. The cartridge or capillary of claim 6, wherein said gel comprises two or more compounds of structure 1.

8. The cartridge or capillary of claim 6, wherein said gel comprises two or more compounds of structure 2.

9. The cartridge or capillary of claim 6, wherein said gel comprises one or more compounds of structure 1 and one or more compounds of structure 2.

10. The cartridge or capillary of claim 6, wherein said gel comprises one or more compounds of structure 2.

11. The cartridge or capillary of claim 6, wherein said gel further comprises polyethylene oxide.

12. The cartridge or capillary of claim 6, wherein said cartridge or capillary is a capillary, which capillary has an interior lumen with walls which are (i) uncoated or (ii) are coated with a coating that (a) does not interfere with CE of said analyte of interest and, (b) prevents resolution of said analyte from degrading over at least 5 runs when said capillary is not conditioned between each run.

13. The cartridge or capillary of claim 6, in which said two or more compounds of structure 1, said mixture of one or more compounds of structure 1 and of one or more compounds of structure 2, or said one or more compounds of structure 2, are present in said gel in a concentration between 0.08% wt/wt and 0.15% wt/wt of the gel.

14. A method for performing electrophoretic separation of labeled analytes, said method comprising:
   (a) loading said analytes onto a gel, which gel comprises an effective amount of
   (A) two or more compounds of structure 1,
   (B) a mixture of one or more compounds of structure 1 and of one or more compounds of structure 2, or (C) one or more compounds of structure 2, wherein said structure 1 is:

and said structure 2 is:

and
(b) subjecting said labeled analytes in said gel to an electric potential, thereby performing an electrophoretic separation of said labeled analytes.

15. The method of claim 14, wherein said gel comprises two or more compounds of structure 1.

16. The method of claim 14, wherein said gel comprises one or more compounds of structure 2.

17. The method of claim 14, wherein said gel comprises one or more compounds of structure 1 and one or more compounds of structure 2.

18. The method of claim 14, wherein said labeled analytes are labeled glycans, optionally wherein said label on said labeled glycans is 8-aminopyrene-1,3,6-trisulfonic acid, trisodium salt (APTS) or 8-Aminonaphthalene-1,3,6-trisulfonic acid (ANTS).

19. The method of claim 14, in which said
(a) two or more compounds of structure 1,
(b) a mixture of one or more compounds of structure 1 and of one or more compounds of structure 2, or
(c) one or more compounds of structure 2, are present in said gel in a concentration between 0.075% wt/wt and 0.15% wt/wt of the gel.

20. The method of claim 14, wherein said gel further comprises polyethylene glycol.

* * * * *